US010765569B2

(12) United States Patent
Chmielewski et al.

(10) Patent No.: US 10,765,569 B2
(45) Date of Patent: Sep. 8, 2020

(54) SYNTHETIC SURFACTANT-FREE FINISH, SHEET HAVING SYNTHETIC SURFACTANT-FREE FINISH, ARTICLES HAVING SHEET WITH SYNTHETIC SURFACTANT-FREE FINISH, AND RELATED METHODS

(71) Applicant: ATTENDS HEALTHCARE PRODUCTS, INC., Greenville, NC (US)

(72) Inventors: Harry J. Chmielewski, Wake Forest, NC (US); Edward L. Seames, Rock Hill, SC (US)

(73) Assignee: ATTENDS HEALTHCARE PRODUCTS, INC., Greenville, NC (US)

( * ) Notice: Subject to any disclaimer, the term of this patent is extended or adjusted under 35 U.S.C. 154(b) by 0 days.

(21) Appl. No.: 15/707,603

(22) Filed: Sep. 18, 2017

(65) Prior Publication Data

US 2018/0000662 A1    Jan. 4, 2018

Related U.S. Application Data

(63) Continuation-in-part of application No. 14/941,252, filed on Nov. 13, 2015, now Pat. No. 9,913,925.

(60) Provisional application No. 62/079,879, filed on Nov. 14, 2014.

(51) Int. Cl.
| | | |
|---|---|---|
| *A61F 13/513* | (2006.01) | |
| *A61F 13/511* | (2006.01) | |
| *A61L 15/32* | (2006.01) | |
| *A61L 15/24* | (2006.01) | |
| *C09D 189/00* | (2006.01) | |
| *A61L 15/62* | (2006.01) | |

(52) U.S. Cl.
CPC ...... *A61F 13/513* (2013.01); *A61F 13/51113* (2013.01); *A61L 15/24* (2013.01); *A61L 15/32* (2013.01); *A61L 15/62* (2013.01); *C09D 189/00* (2013.01)

(58) Field of Classification Search
None
See application file for complete search history.

(56) References Cited

U.S. PATENT DOCUMENTS

| | | | |
|---|---|---|---|
| 5,912,194 A | 6/1999 | Everhart et al. | |
| 5,938,649 A | 8/1999 | Ducker et al. | 604/363 |
| 5,944,705 A | 8/1999 | Ducker et al. | 604/364 |
| 6,459,014 B1 | 10/2002 | Chmielewski et al. | 604/360 |
| 6,936,345 B2 | 8/2005 | Wild et al. | 428/375 |
| 9,913,925 B2* | 3/2018 | Chmielewski | A61F 13/51113 |
| 2003/0087982 A1 | 5/2003 | Kanazawa | |
| 2004/0158213 A1 | 8/2004 | Ponomarenko et al. | 604/367 |
| 2006/0178650 A1 | 8/2006 | Hakansson et al. | 604/378 |
| 2009/0156974 A1 | 6/2009 | Truelsen et al. | 602/45 |
| 2010/0228211 A1 | 9/2010 | Becker et al. | 604/366 |
| 2010/0280479 A1 | 11/2010 | Svensson et al. | 604/385.23 |
| 2011/0092933 A1 | 4/2011 | Canales Espinosa de los Monteros et al. | 604/359 |
| 2016/0136321 A1* | 5/2016 | Chmielewski | A61F 13/51113 252/380 |

FOREIGN PATENT DOCUMENTS

| | | |
|---|---|---|
| CN | 101324029 | 12/2008 |
| CN | 201286802 | 8/2009 |
| JP | H 11172578 | 6/1999 |
| JP | H 11350352 | 12/1999 |
| JP | 2010110546 | 5/2010 |
| RU | 2314081 | 5/2005 |
| WO | WO 01/48065 | 7/2001 |
| WO | WO 2014066297 | 5/2014 |

OTHER PUBLICATIONS

International Search Report and Written Opinion issued in PCT/US2015/060709, dated Jan. 28, 2016.
Kumar et al., "Preparation and characterization of bio-nanocomposite films based on soy protein isolate and montmorillonite using melt extrusion", Journal of Food Engineering, 100: 480-489, 2010.
Salas et al., "Water-Wettable Polypropylene Fibers by Facile Surface Treatment Based on Soy Proteins", ACS Appl. Mater. Interfaces 2013, V5, pp. 6541-6548.
Extended European Search Report Issued in Corresponding to European Application No. 15858898.8, dated Apr. 4, 2018.
Goli, et al., "Functional Retrieved from Internet Coatings Based on Denaturation and Adsorption of Proteins," Abstract Retrieved from Internet http://repository.lib.ncsu.edu/bitstream/handle/1840.16/7785/etd.pdf.
Goli, et al., "Generation of Functional Coatings on Hydrophobic Surfaces Through Deposition of Denatured Proteins Followed by Grafting from Polymerization," Biomacromolecules, 13(5): 1371-1382, 2012.
Hefnawy, et al., "Physicochemical Characteristics of Soy Protein Isolate and Fenugreek Gum Dispersed Systems," Journal of Food and Science and Technology, 48(3): 371-377, 2011.
Wagner, et al., "Influence of Denaturation, Hydrophobicity, and Sulfhydryl Content on Solubility and Water Absorbing Capacity of Soy Protein Isolates," Journal of Food Science, 55(3), 765-770, 1990.
Office Action Issued in Corresponding Chinese Patent Application No. 201580072147.4, dated Feb. 6, 2020.
Office Action Issued in Corresponding Japanese Patent Application No. 2017544852, dated Nov. 21, 2019. English Translation.
Office action and Search Report issued in Corresponding Russian App. No. 2017120483, dated Apr. 10, 2019 (English translation).

* cited by examiner

*Primary Examiner* — Patricia L. Hailey
*Assistant Examiner* — Colette B Nguyen
(74) *Attorney, Agent, or Firm* — Norton Rose Fulbright US LLP

(57) ABSTRACT

Nonwoven (and film) topsheet and acquisition/distribution materials treated with a hydrophilic, synthetic surfactant-free finish, absorbent articles for infant or incontinence care that contain these materials, and methods for apply such finishes and/or making such absorbent articles.

12 Claims, 12 Drawing Sheets

| No. | Finish | Pre-mix | | | Mix | | | Solution pH | | Cook | | Appearance of Solution | |
|---|---|---|---|---|---|---|---|---|---|---|---|---|---|
| | | Temp | % Solids | Shear | Temp | % Solids | Shear | Before adjust | After adjust | Temp | Time | At 90 C. | At 22 C. |
| 1 | SPI 100 | 90 | 0.25% | High | 90 | 0.125% | Low | 2.3 | 8.0 | 90 | 60 | Cloudy | Precipitate |
| 2 | | -- | -- | -- | 80 | 0.5% | High | 2.6 | 8.0 | 80 | 30 | Cloudy | Precipitate |
| 3 | | 22 | 1% | High | 22 | 0.5% | Low | 2.7 | 8.0 | 90 | 60 | Clear | Hazy |
| 4 | | -- | -- | -- | 22 | 0.5% | High | 2.5 | 8.2 | 80 | 30 | Clear | Hazy |
| 5 | | -- | -- | -- | 80 | 0.5% | High | 2.5 | -- | 80 | 30 | Clear | Clear |

FIG. 2

| Sample | Solution Concent-ration | Mix Temp | Application Temp | Wet Pick Up (g soln / g NW) | Add-On (g solids/g NW x 100) | Average Drop Value |
|---|---|---|---|---|---|---|
| 0 | -- | -- | -- | -- | -- | 0.4 |
| 3 | 0.4% | 22 C. | 22 C. | 1.03 | 0.4% | 0.7 |
| 9 | 0.4% | 50 C. | 22 C. | 0.97 | 0.4% | 1.1 |
| 6 | 0.4% | 70 C. | 22 C. | 0.97 | 0.4% | 0.7 |
| 2 | 0.8% | 22 C. | 22 C. | 0.92 | 0.7% | 1.0 |
| 8 | 0.8% | 50 C. | 22 C. | 0.85 | 0.7% | 1.4 |
| 5 | 0.8% | 70 C. | 22 C. | 0.95 | 0.8% | 1.4 |
| 8 | 0.8% | 80 C. | 22 C. | 0.76 | 0.6% | 1.5 |
| 7 | 0.8% | 80 C. | 50 C. | 0.93 | 0.7% | 2.0 |
| 6 | 0.8% | 80 C. | 70 C. | 0.88 | 0.7% | 1.9 |
| 1 | 1.2% | 22 C. | 22 C. | 1.05 | 1.3% | 0.8 |
| 7 | 1.2% | 50 C. | 22 C. | 0.72 | 0.9% | 1.0 |
| 4 | 1.2% | 70 C. | 22 C. | 1.07 | 1.3% | 1.7 |
| 5 | 1.2% | 80 C. | 22 C. | 1.71 | 2.1% | 2.0 |
| 4 | 1.2% | 80 C. | 40 C. | 1.71 | 2.1% | 2.0 |
| 3 | 1.2% | 80 C. | 50 C. | 1.73 | 2.1% | 2.0 |
| 2 | 1.2% | 80 C. | 60 C. | 1.75 | 2.1% | 2.0 |
| 1 | 1.2% | 80 C. | 70 C. | 1.55 | 1.9% | 1.9 |

FIG. 3

| Topsheet Finish | Dose | Liquid Runoff (g.) | Liquid Travel (mm) |
|---|---|---|---|
| Commercial Semi-durable Surfactant | 1 | 3.7 | 0 |
| | 2 | 3.6 | 0 |
| | 3 | 4.1 | 0 |
| | 4 | 14 | 8 |
| | 5 | 36 | 12 |
| | 6 | 39 | 29 |
| Prototype at 0.006 g. SPI / g. nonwoven | 1 | 1.2 | 0 |
| | 2 | 1.3 | 0 |
| | 3 | 1.6 | 0 |
| | 4 | 15 | 17 |
| | 5 | 23 | 21 |
| | 6 | 18 | 20 |

FIG. 6

| LAB TEST | DOSE | COMMER-CIAL FLUFF/SAP BABY DIAPER | EXAMPLE 1 12 gsm SPUNBOND | | EXAMPLE 2 15 gsm SMS | |
|---|---|---|---|---|---|---|
| | | | No Finish | 0.006 g. SPI / g. NW | No Finish | 0.008 g. SPI / g. NW |
| ACQ/REW | ACQ1 (sec) | 23 | 23 | 23 | 28 | 24 |
| | ACQ2 | 22 | 23 | 20 | 97 | 22 |
| | ACQ3 | 22 | 29 | 21 | 35 | 24 |
| | ACQ4 | 24 | 31 | 22 | 38 | 23 |
| | REW2 (g) | 0.1 | 0.0 | 0.1 | 0.1 | 0.0 |
| | REW3 | 0.1 | 0.0 | 0.7 | 0.0 | 0.1 |
| | REW4 | 0.2 | 0.1 | 1.0 | 0.1 | 1.3 |
| | PW2 (g) | 0.040 | 0.013 | 0.003 | 0.013 | 0.000 |
| | PW3 | 0.013 | 0.000 | 0.010 | 0.003 | 0.003 |
| | PW4 | 0.017 | 0.037 | 0.037 | 0.017 | 0.013 |
| | LEAKAGE (g) | 0.1 | 4.3 | 0.1 | 4.6 | 2.6 |
| ANAREWET | ACQ1 (sec) | 38 | 32 | 31 | 82 | 47 |
| | ACQ2 | 60 | 55 | 52 | 73 | 63 |
| | ACQ3 | 101 | 103 | 92 | 123 | 113 |
| | ACQ4 | 198 | 191 | 230 | 251 | 232 |
| | LEAKAGE (g) | 10.1 | 8.0 | 0.6 | 4.7 | 0.0 |
| RUNOFF II | RUNOFF1 (g) | 25 | 18 | 14 | 59 | 65 |
| | RUNOFF2 | 40 | 43 | 0.9 | 68 | 52 |
| | RUNOFF3 | 55 | 46 | 2.7 | 71 | 45 |
| | RUNOFF4 | 65 | 47 | 0.1 | 71 | 23 |
| Mannequin Leakage | ABL (g) | 206 | | 250 | | |

FIG. 7

| Dose | Control Nonwoven ||||  SPI-Treated Nonwoven ||||
|---|---|---|---|---|---|---|---|---|
| | Liquid Acquisition Time (sec) | Rewet (g) | Surface Wetness (g) | Side Leakage (g) | Liquid Acquisition Time (sec) | Rewet (g) | Surface Wetness (g) | Side Leakage (g) |
| 1 | 26 ± 1.2 | -- | -- | -- | 24 ± 3.5 | -- | -- | -- |
| 2 | 21 ± 1.7 | 0.1 ± 0.02 | 0.007 | -- | 18 ± 2.1 | 0.1 ± 0.02 | 0.010 | -- |
| 3 | 22 ± 1.5 | 0.4 ± 0.17 | 0.027 | -- | 18 ± 2.1 | 0.7 ± 0.4 | 0.017 | -- |
| 4 | 23 ± 1.5 | 1.8 ± 0.57 | 0.050 | 2.6 | 20 ± 4.0 | 2.3 ± 1.2 | 0.013 | 1.5 |

FIG. 8

| Dose | Control Nonwoven ||||  SPI-Treated Nonwoven ||||
|---|---|---|---|---|---|---|---|---|
| | Liquid Acquisition Time (sec) | Rewet (g) | Surface Wetness (g) | Side Leakage (g) | Liquid Acquisition Time (sec) | Rewet (g) | Surface Wetness (g) | Side Leakage (g) |
| 1 | 26 ± 1.2 | -- | -- | -- | 21 ± 1.5 | -- | -- | -- |
| 2 | 21 ± 1.7 | 0.1 ± 0.02 | 0.007 | -- | 18 ± 2.7 | 0.1 ± 0.02 | 0.007 | -- |
| 3 | 22 ± 1.5 | 0.4 ± 0.17 | 0.027 | -- | 18 ± 3.5 | 1.2 ± 0.77 | 0.020 | -- |
| 4 | 23 ± 1.5 | 1.8 ± 0.57 | 0.050 | 2.6 | 18 ± 3.2 | 2.8 ± 0.68 | 0.027 | 3.0 |

| Dose | Control Nonwoven | | | | SPI-Treated Nonwoven | | | |
|---|---|---|---|---|---|---|---|---|
| | Liquid Acquisition Time (sec) | Rewet (g) | Surface Wetness (g) | Side Leakage (g) | Liquid Acquisition Time (sec) | Rewet (g) | Surface Wetness (g) | Side Leakage (g) |
| 1 | 26 ± 1.2 | -- | -- | -- | 26 ± 1.0 | -- | -- | -- |
| 2 | 21 ± 1.7 | 0.1 ± 0.02 | 0.007 | -- | 18 ± 2.3 | 0.5 ± 0.02 | 0.003 | -- |
| 3 | 22 ± 1.5 | 0.4 ± 0.17 | 0.027 | -- | 18 ± 3.0 | 0.6 ± 0.56 | 0.007 | -- |
| 4 | 23 ± 1.5 | 1.8 ± 0.57 | 0.050 | 2.6 | 21 ± 2.5 | 2.7 ± 1.63 | 0.003 | 1.5 |

FIG. 11

| Dose | Control Nonwoven | | | | SPI-Treated Nonwoven | | | |
|---|---|---|---|---|---|---|---|---|
| | Liquid Acquisition Time (sec) | Rewet (g) | Surface Wetness (g) | Side Leakage (g) | Liquid Acquisition Time (sec) | Rewet (g) | Surface Wetness (g) | Side Leakage (g) |
| 1 | 26 ± 1.2 | -- | -- | -- | 24 ± 7.4 | -- | -- | -- |
| 2 | 21 ± 1.7 | 0.1 ± 0.02 | 0.007 | -- | 20 ± 2.6 | 0.0 ± 0.01 | 0.003 | -- |
| 3 | 22 ± 1.5 | 0.4 ± 0.17 | 0.027 | -- | 21 ± 5.5 | 0.4 ± 0.23 | 0.000 | -- |
| 4 | 23 ± 1.5 | 1.8 ± 0.57 | 0.050 | 2.6 | 20 ± 3.1 | 1.3 ± 1.11 | 0.000 | 0.04 |

| | Dose | Control Nonwoven | | | | SPI-Treated Nonwoven | | | |
|---|---|---|---|---|---|---|---|---|---|
| | | Liquid Acquisition Time (sec) | Rewet (g) | Surface Wetness (g) | Side Leakage (g) | Liquid Acquisition Time (sec) | Rewet (g) | Surface Wetness (g) | Side Leakage (g) |
| 22° C. | 1 | 29 ± 1.5 | -- | -- | -- | 25 ± 1.0 | -- | -- | -- |
| | 2 | 24 ± 1.5 | 0.1 ± 0.01 | 0.01 | -- | 20 ± 1.0 | 0.1 ± 0.01 | 0.01 | -- |
| | 3 | 31 ± 2.1 | 0.1 ± 0.07 | 0.07 | -- | 21 ± 1.0 | 0.4 ± 0.27 | 0.01 | -- |
| | 4 | 38 ± 1.2 | 1.4 ± 1.64 | 0.08 | 1.8 | 23 ± 1.0 | 3.7 ± 0.65 | 0.02 | 0.12 |
| 37° C. | 1 | 19 ± 0.0 | -- | -- | -- | 19 ± 0.6 | -- | -- | -- |
| | 2 | 17 ± 2.7 | 0.1 ± 0.00 | 0.14 | -- | 17 ± 2.7 | 0.1 ± 0.03 | 0.17 | -- |
| | 3 | 20 ± 4.4 | 0.2 ± 0.11 | 0.11 | -- | 18 ± 3.2 | 0.7 ± 0.42 | 0.08 | -- |
| | 4 | 26 ± 3.5 | 1.3 ± 2.00 | 0.10 | 0.8 | 20 ± 3.8 | 2.6 ± 0.75 | 0.08 | 0.00 |

FIG. 12

|  | Dose | Anarewet Liquid Acquisition Time (sec) | |
|---|---|---|---|
|  |  | Control Nonwoven | SPI-Treated Nonwoven |
| 22° C. | 1 | 46 ± 1.5 | 46 ± 4.4 |
|  | 2 | 71 ± 3.0 | 76 ± 2.7 |
|  | 3 | 132 ± 8.9 | 137 ± 24.0 |
|  | 4 | 271 ± 29.1 | 231 ± 57.3 |
| 37° C. | 1 | 38 ± 2.7 | 36 ± 1.4 |
|  | 2 | 60 ± 4.4 | 60 ± 1.5 |
|  | 3 | 141 ± 43.0 | 97 ± 3.5 |
|  | 4 | 261 ± 64.1 | 224 ± 71.1 |

FIG. 13

| Dose Volume (ml) | Dose No. | Run-Off (g) | |
|---|---|---|---|
|  |  | Control Nonwoven | SPI-Treated Nonwoven |
| 35 | 1 | 0.1 ± 0.1 | 0.2 ± 0.2 |
|  | 2 | 0.2 ± 0.1 | 0.0 ± 0.0 |
|  | 3 | 0.3 ± 0.2 | 0.1 ± 0.1 |
| 70 | 1 | 5.9 ± 5.3 | 2.8 ± 2.1 |
|  | 2 | 3.2 ± 4.5 | 0.0 ± 0.0 |
|  | 3 | 11.7 ± 9.3 | 8.0 ± 2.8 |
| 105 | 1 | 5.1 ± 3.8 | 7.5 ± 4.2 |
|  | 2 | 2.5 ± 1.2 | 5.1 ± 7.7 |
|  | 3 | 25.8 ± 9.2 | 21.2 ± 8.6 |

FIG. 14

| Nonwoven Finish | Solution pH | DROP VALUE | |
|---|---|---|---|
| | | Initial | After warm tap water rinse (200 ml) |
| Semi-durable surfactant | -- | 2 | 0 |
| Arcon SM | 8.2 | 2 | 1 |
| Arcon S | 7.6 | 2 | 1 |
| Pro-Fam 974 | 7.4 | 2 | 1 |
| 7B Soy Flour | 6.6 | 2 | 1 |

FIG. 15

SYNTHETIC SURFACTANT-FREE FINISH, SHEET HAVING SYNTHETIC SURFACTANT-FREE FINISH, ARTICLES HAVING SHEET WITH SYNTHETIC SURFACTANT-FREE FINISH, AND RELATED METHODS

CROSS REFERENCE TO RELATED APPLICATION

This application is a continuation-in-part of U.S. patent application Ser. No. 14/941,252, filed Nov. 13, 2015, which claims priority to U.S. Provisional Patent Application No. 62/079,879, filed Nov. 14, 2014, both of which are incorporated herein by reference in their respective entireties.

FIELD OF INVENTION

The present invention relates generally to disposable absorbent products such as infant diapers, adult incontinence briefs, pull-up underwear, bladder control pads, bedpads; and, more particularly, but not by of limitation, to nonwoven topsheet and acquisition/distribution layers (ADL's) finished with durable, hydrophilic, synthetic surfactant-free finishes, and to absorbent products that contain topsheets and ADL's treated with a synthetic surfactant-free finish. The present synthetic surfactant free-finishes, and the methods of applying it, can also be useful for woven materials comprising hydrophobic fibers that require a hydrophilic finish.

BACKGROUND

Absorbent articles, such as baby diapers, training pants, adult incontinence products and other such absorbent products include a topsheet that is closest to the wearer, an outer, moisture-impermeable backsheet, and an absorbent core. Disposable absorbent products have met with widespread acceptance in the marketplace for a variety of applications, including infant and adult incontinence care, in view of the manner in which such products can provide effective and convenient liquid absorption and retention while maintaining the comfort of the wearer. However, experience has shown that a need exists for more skin-friendly topsheet nonwovens. Examples of absorbent article constructions with which the present sheets can be used are disclosed in United States Patent Application Publications No. US 2006/0178650 and No. US 2010/0280479.

The nondurable, or fugitive, nature of synthetic surfactants used on all polyolefin topsheets and acquisition/distribution layers in use today play a role in absorbent product acquisition and rewet performance, but have a potential to compromise skin health. Synthetic surfactants are used as penetration aids in transdermal drug delivery. Synthetic surfactants washed from the nonwoven fibers during product use can increase the permeability of stratum corneum to all potential irritants, including the synthetic surfactant itself. Various emollient materials have be used in an attempt to restore barrier function to damaged skin, but a straightforward solution to the problem is to eliminate all synthetic surfactant from the nonwoven. In this invention we have identified potential chemistries for imparting wettability to polyolefin nonwovens and films, and teach how they can be applied effectively—without the use of any conventional synthetic surfactants and with the goal of promoting skin health.

Nonwovens made from polypropylene are hydrophobic. By application of suitable finishing treatments, it is possible to impart semi-durable hydrophilic properties to the nonwoven to achieve performance in liquid strike-through and liquid runoff that is required for their use in absorbent products. Suitable finishing treatments are typically proprietary blends of synthetic surfactant solutions which are commercially available, for example, from Schill & Seilacher AG (e.g. Silastol PHP 26, Silastol PHP 90, & Silastol 163), and Pulcra Chemicals (e.g. Stantex S 6327, Stantex S 6087-4, & Stantex PP 602). They are typically applied to spunbond nonwovens in the range of 0.004-0.006 gm solids/gm nonwoven (i.e. 0.4-0.6% wt/wt). An example of a synthetic surfactant that has been used widely used in commercially-available topsheet finishes would be Triton GR-5M, an anionic sulfosuccinate surfactant manufactured by Dow Chemical Company. Other types of surfactants used are based on fatty acid polyethylene glycol esters.

U.S. Pat. Nos. 5,938,649 and 5,944,705, Ducker, et al., disclosed an absorbent article containing aloe vera on the surface of the article contacting the wearer's skin to reduce rash. A preferred embodiment of this invention was an essentially water-free aloe vera in a waterless lubricant that was applied to an absorbent product independently of any surfactant finish on the topsheet nonwoven. Procter & Gamble commercialized a baby diaper in the late 1990's/early 2000's that contained an emollient lotion, applied in stripes, on a conventional topsheet nonwoven. U.S. Pat. No. 6,459,014 B1, Chmielewski and Erdman, mentions pH control agents such as citric acid and sodium citrate that can be added to a nonwoven topsheet in conjunction with an optional surfactant. However, all examples in this patent included synthetic surfactant and there was no discussion of how a nonwoven could be successfully treated with a surfactant-free solution of citric acid, or whether it could impart useful hydrophilic properties to the nonwoven. Furthermore, citric acid and sodium citrate are freely soluble in saline solution and would not provide a sufficiently durable finish to a topsheet nonwoven. More recently, in U.S. Pat. No. 6,936,345 B2, Wild et. al. describe a process for finishing nonwovens in such a way to meet requirements in regard to the permanence of the hydrophilic finish and be capable of providing an additional benefit, in this case suppression of the growth of bacteria. They described an aqueous antimicrobial finish containing a monoester of glycerol, a fatty acid and chitosan. The monoester of glycerol and the fatty acid are surface active ingredients that facilitate spreading of the antimicrobial finish on the nonwoven in the finishing process.

Salas, et al. in "Water-Wettable Polypropylene Fibers by Facile Surface Treatment Based on Soy Proteins", ACS Appl. Mater. Interfaces 2013, 5,6541-6548, reported on the modification of the wetting behavior of polypropylene nonwovens after adsorption of soybean proteins. Using Quartz Crystal Microgravimetry with thin, flat films of polypropylene, they confirmed a high affinity of adsorption for soy protein on polypropylene. A fast initial adsorption occurred in the order of seconds. This showed that adsorption of soy protein will indeed occur on polypropylene if the protein solution is forced to be in contact with the polymer surface. When extending their work to a polypropylene nonwoven, they noted that the hydrophobic nonwoven floated on the surface of the protein solution and prevented effective adsorption of the protein. To overcome this issue, they first immersed the polypropylene nonwovens in 2-propanol to clean the nonwoven, followed by an immersion into 1 mg/mL 2-propanol solution of cationic dioctadecyldimethylammonium bromide surfactant.

SUMMARY

A novel nonwoven or film topsheet or other acquisition/distribution materials that has a hydrophilic, synthetic surfactant-free finish that is useful for absorbent products for infant or incontinence care that contain these materials. These materials are made by intimately treating the raw unfinished materials in the absence of air bubbles with an aqueous solution of a hydrophilic, synthetic surfactant-free finish and then drying the materials.

Some embodiments of the present hydrophilic, synthetic sheets comprise: a sheet of synthetic material having a first surface; where the sheet comprises a hydrophilic finish including molecules of a water-soluble proteins dispersed on the first surface; and where the finish is substantially free of synthetic surfactants. Non-limiting examples of water-soluble proteins include ProFam® 974 ProFam® 781, Clarisoy® 100, Clarisoy® 150, Clarisoy® 1900, Arcon S Arcon SM, 7B Soy Flour, Bakers Soy Flour, and Bakers Soy Flour all of which are commercially available from Archer Daniels Midland (ADM, Decatur, Ill.), and Prolia® defatted soy flours, commercially available from Cargill Incorporated (Minneapolis Minn.). In some embodiments, the finish does not include synthetic materials capable of reducing the surface tension of water below 50 milliNewtons/m (mN/m). In some embodiments, the sheet comprises a nonwoven fabric or a film. In some embodiments, the sheet is a topsheet of an absorbent article. In some embodiments, the sheet is a distribution-acquisition layer of an absorbent article. In some embodiments, the water-soluble protein comprises a thermally-denatured protein. In some embodiments, a 0.4-1.2% aqueous solution of the water-soluble protein has a surface tension greater than 50 milliNewtons per meter (mN/m). In some embodiments, a 0.5-10% aqueous solution of the water-soluble protein has a surface tension less than 49 milliNewtons per meter (mN/m). In some embodiments, a 0.5-1.2% aqueous solution of the water-soluble protein has a surface tension less than 49 milliNewtons per meter (mN/m). In some embodiments, at least 0.004 grams of the molecules of the water-soluble protein are dispersed on the sheet for each gram of sheet.

Some embodiments of the present disposable absorbent articles comprises; a topsheet comprising an embodiment of the present hydrophilic, synthetic sheets; a backsheet; and an absorbent core disposed between the topsheet and the backsheet.

Some embodiments of the present disposable absorbent articles comprise; a topsheet; a distribution-acquisition layer comprising an embodiment of the present hydrophilic, synthetic sheets; a backsheet; and an absorbent core disposed between the distribution-acquisition layer and the backsheet.

Some embodiments of the present methods (e.g., of imparting hydrophilic properties to a sheet of polymeric material) comprise: applying an aqueous solution of a water-soluble protein to a sheet of polymeric material in an aqueous solution; and drying the sheet such that at least a portion of the protein is retained on a surface of the sheet; where the aqueous solution is substantially free of synthetic surfactants. In some embodiments, the sheet includes less than 0.1, less than 0.05, less than 0.01, less than 0.001 wt. % synthetic surfactants, or no synthetic surfactants. In a particular embodiment, no synthetic surfactants are included. In some embodiments, at least a portion of the water-soluble protein is thermally-denatured. In some embodiments, the sheet comprises a nonwoven fabric or a film.

Some embodiments of the present methods further comprise, prior to applying the aqueous solution to the sheet: admixing the water-soluble protein in water; heating the water to a temperature of between 40 degrees Celsius (° C.) and 99° C.; and stirring the admixture to dissolve the protein in the water. In some embodiments, the water is heated before admixing the water-soluble protein. In some embodiments, the temperature of the water is maintained between 40° C. and 99° C. during at least a portion of the stirring. In some embodiments, the temperature of the water is maintained between 40° C. and 99° C., or 50 to 85° C. for a period of time sufficient to thermally denature at least a portion of the protein. Some embodiments further comprise: adjusting the pH of the admixture of water and protein prior to heating the temperature of the admixture.

In some embodiments of the present methods, the temperature of the solution is between 20° C. and 40° C. during at least a portion of applying the aqueous solution to the sheet.

In some embodiments of the present methods, applying the aqueous solution to the sheet comprises: immersing the sheet a first time in the solution; and immersing the sheet a second time in the solution. Some embodiments further comprise: calendaring the sheet between immersing the sheet the first time and immersing the sheet the second time.

In some embodiments of the present methods, applying the aqueous solution to the sheet is performed with at least one coating apparatus selected from the group consisting of: a slot die, a knife coater, a kiss coater, a gravure printer, a multiple-roller coating apparatus, and a screen coating apparatus.

In some embodiments of the present methods, the aqueous solution comprises a preservative. In some embodiments, the preservative comprises one or more preservatives selected from the group consisting of elemental silver (e.g., MicroSilver), Japanese honeysuckle (e.g., Plantservative), one or more tocopherols (e.g., Nutrabiol), or mixtures thereof.

In some embodiments of the present methods, the protein comprises soy protein isolate (SPI).

Some embodiments of the present finishes (e.g., for a synthetic nonwoven or film) can include: an aqueous solution of a water-soluble, thermally-denatured protein, the solution having a surface tension greater than 50 milliNewtons per meter (mN/m). In some embodiments, the aqueous solution comprises a preservative. In some embodiments, the preservative comprises one or more preservatives selected from the group consisting of: Plantservative, MicroSilver, and Nutrabiol.

Some embodiments of the present finishes (e.g., for a synthetic nonwoven or film) can include: an aqueous solution of a water-soluble, thermally-denatured protein, the solution having a surface tension less than 49 milliNewtons per meter (mN/m). In some embodiments, the aqueous solution comprises a preservative. In some embodiments, the preservative comprises one or more preservatives selected from the group consisting of elemental silver (e.g., MicroSilver), Japanese honeysuckle (e.g., Plantservative), one or more tocopherols (e.g., Nutrabiol), The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "absorbent article" and "absorbent garment" are used in this disclosure to refer to garments or articles that are configured to absorb and contain exudates and, more specifically, refer to garments or articles that are placed against or in proximity to the body of a wearer to absorb and contain the exudates discharged from the wearer's body. Examples of such absorbent articles or absorbent garments include diapers, training pants, feminine hygiene products, bibs, wound dressing, bed pads, and adult incontinence products. The term "disposable" when used with "absorbent article" or "absorbent garment" refers to garments and articles that are intended to be discarded after a single use.

"Absorbent core" is used in this disclosure to refer to a structure positioned between a topsheet and backsheet of an absorbent article for absorbing and containing liquid received by the absorbent article. An absorbent core can comprise one or more substrates, absorbent polymer material, adhesives, and/or other materials to bind absorbent materials in the absorbent core.

A device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 2-3 depict tables of various characteristics of the present sheets and/or finishes.

FIG. 6-15 depict tables of various characteristics of the present sheets and/or finishes.

DETAILED DESCRIPTION OF ILLUSTRATIVE EMBODIMENTS

Figure 1:
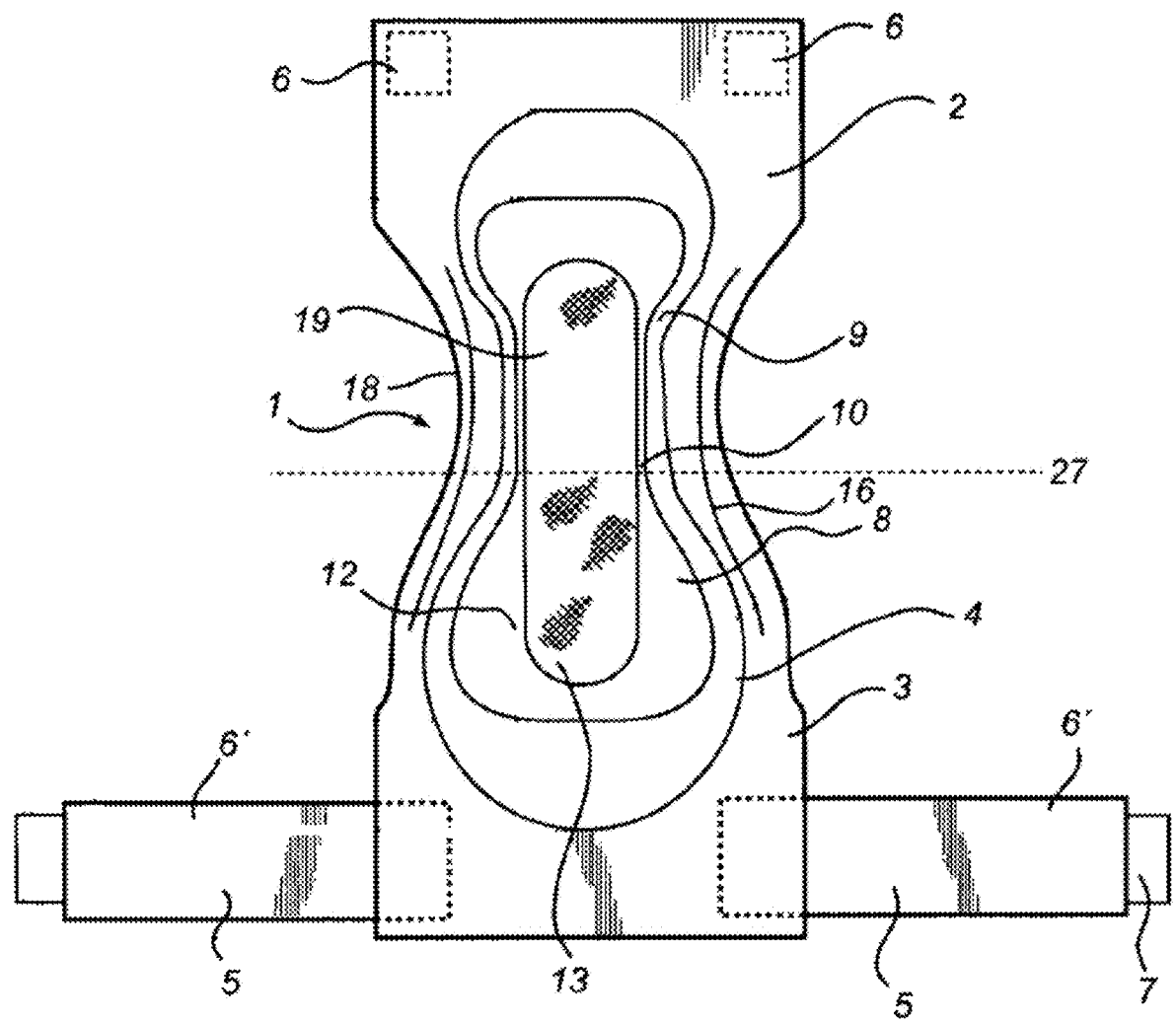
FIG. 1 depicts a plan view of one example of the present absorbent articles.

Referring now to the drawings, and more particularly to FIG. 1, shown therein and designated with the reference numeral 1 is an example of the present absorbent articles. In the embodiment shown, article 1 includes a front portion 2, a rear portion 3, a core portion 4, and band portions 5. In this embodiment, absorbent article 1 is configured as a diaper; in other embodiments, the present absorbent articles can be configured as pads and/or the like.

In the embodiment shown, front portion 2 includes fasteners 6 (e.g., adhesive, hook-and-loop patches, or other fastening structure) and band portions 5 include fasteners 6' and 7 (e.g., adhesive, hook-and-loop patches, or other fastening structure). In this embodiment, article 1 comprises an absorbent core 8 with an outer zone 9 and a middle zone 10. In the embodiment shown, article 1 also comprises a second absorbent core 12; other embodiments may include only a single absorbent core. In this embodiment, article 1 further comprises a distribution-acquisition layer 13 that spans at least absorbent core 8 (e.g., and absorbent core 12).

In the embodiment shown, article 1 is bounded by a back sheet 18 (that faces outward when worn) and a top sheet 19 (that abuts a wearer's skin when worn). In this embodiment, top sheet 19 and back sheet 18 are co-extensive and have dimensions larger than those of the absorbent core. Back sheet 18 typically prevents liquid absorbed and contained in the absorbent core from wetting articles (e.g., clothing) that contact absorbent article 1. In many (if not all) embodiments, back sheet 18 is impervious to liquids and can comprise a thin plastic (e.g., polyethylene) film, although other flexible liquid impervious materials may also be used. In some embodiments, back sheet 18 may be "breathable" or configured to permit vapors to escape from the absorbent core while preventing exudates from passing through back sheet 18.

In the depicted embodiment, top sheet 19 is joined with and superimposed on the back sheet 18 thereby forming the periphery of article 1. In some embodiments, top sheet 19 is compliant, soft feeling, and non-irritating to the wearer's skin. In many (if not all) embodiments, top sheet 19 is liquid pervious permitting liquids to readily penetrate through its thickness. Top sheet 19 can be manufactured from a wide range of materials such as porous foams, reticulated foams, apertured plastic films, natural fibres (e.g., wood or cotton fibres), synthetic fibres (e.g., polyester, polyethen or polypropylene fibres) or from a combination of natural and synthetic fibres. In some embodiments, top sheet 19 includes both hydrophilic and hydrophobic material (e.g., positioned in different zones to meet different demands, such as, for example, to isolate a wearer's skin from liquids in the absorbent core). In various embodiments, top sheet 19 may be woven, non-woven, spun bonded, carded, or the like.

In the embodiment shown, fluid acquisition-distribution layer 13 is configured to collect and temporarily hold discharged body fluid. For example, a portion of discharged fluid may (e.g., depending upon the wearer's position) permeate acquisition-distribution layer 13 and be absorbed by the absorbent region in the area proximate to the discharge. However, since fluid is often discharged in gushes, the portion of the absorbent core in such area may not absorb the fluid as quickly as it is discharged, and the acquisition-distribution layer is configured to transport fluid from the point of initial fluid contact to other parts of the acquisition-distribution layer for absorption by the absorbent core.

As described below, the present finishes and methods enable the manufacture of synthetic surfactant-free hydrophilic sheets that are suitable for use as a topsheet (e.g., 19) and/or as an acquisition-distribution layer (e.g., 13) in absorbent articles (e.g., 1). As described in more detail below, the present finishes and methods involve the application of denatured proteins to sheets comprising hydrophobic material (e.g., films or nonwovens) to impart hydrophilic properties. In general, the present finishes comprise proteins in solution and the present methods involve applying the solution to a sheet to distribute the proteins, and subsequently drying the sheet such that the proteins are deposited on the sheet.

I. Solution Properties of Soy Protein Isolate (SPI)

The effects of temperature and pH were investigated on solutions of soy protein isolate (SPI) prepared via a concentrated pre-mix, mix, and cook protocol. Elevated temperatures were used in an attempt to at least partially denature the protein and promote adhesion and durability to the nonwoven finish. Properties of proteins that promote adhesion and durability to nonwoven fibers are related to properties that can lead to an undesirable effect of biofouling in medical devices upon exposure of hydrophobic polymer surfaces to protein solutions. In some embodiments, the pH of the solution can be adjusted to be between 7.0 to 8.5, or about 7.5 to 8.0. In some embodiment, the solution containing the SPI has a pH of 7.0 to 8.5 (for example, a solution of ProFAM® 781) so no pH adjustment is necessary. The SPI (e.g., Clarisoy® 100) can be dispersed either in water at room or elevated temperature to form clear solutions while other SPIs (e.g., ProFAM® 781) can form cloudy solutions. The examples and FIGS. described in Sections I to IX relate to Clarisoy® 100 or other water-soluble soy proteins however, it should be understood that the same or similar results are expected in each section for all water-soluble soy proteins described herein, except for ProFam® 781 surface tension values, which are described in Section XI.

FIG. 2 shows certain properties of various mixtures made with the Clarisoy® 100 SPI, a 100% water-soluble SPI, and the methods by which those mixtures were made. As shown, Solution No. 1 was prepared by first premixing 0.25% solids of SPI in 90° C. distilled water at high shear until the soy powder was uniformly dispersed in the liquid. The solution was then diluted with an equal volume of 90° C. distilled water and mixed under low shear for about 10 minutes. Before the "cook" stage, the pH of the mixture was adjusted to pH 8 with 0.1 N NaOH. Following the pH adjustment, the mixture was "cooked" or maintained at an elevated temperature with low-shear mixing for 60 minutes to simulate use of the mixture in a commercial process. The appearance of this mixture was cloudy at 90° C. After cooling to 22° C., a precipitate settled from the mixture, indicating the presence of undissolved solids. Formation of a precipitate was associated with adjustment of pH while the dispersion was at an elevated temperature. When solutions are prepared without pH adjustment, the SPI can be dispersed either in water at room or elevated temperature to form clear solutions. It was also determined that comparable solution properties were achieved when the pre-mix was eliminated and the cook time reduced to the time required to bring the solution to temperature (see mixtures No. 3 and 4). The mixture that formed a precipitate may not be the best for obtaining the desired finish on nonwovens. Because of the differences in solution properties indicated above, the investigation of the ability of SPI to impart a hydrophilic finish to nonwovens was focused on solutions mixed at elevated temperature both with and without prior modification of solution pH. In experiments in which pH was adjusted, the SPI was dispersed in water at room temperature before mixing at elevated temperature.

II. Hydrophilicity as a Function of Mixing and Application Temperatures of Solutions Heating a solution of SPI prior to application on a nonwoven has been shown to improve the performance of the nonwoven on an absorbent product. Heating soy proteins causes dissociation of their quaternary structures, denatures their subunits, and promotes the formation of protein aggregates via electrostatic, hydrophobic and disulphide interchange mechanisms. In addition to heating, the adjustment of pH and ionic strength, hydrolysis, and covalent attachment of other constituents would be expected to modify the performance of a nonwoven treated with an SPI finish. In some embodiments, adjustment of the pH is not necessary. The hydrophilicity of a nonwoven treated with SPI as function of mix temperature, application temperature, and soy protein solids add-on has been summarized in FIG. 3.

The nonwoven was a 12.5 gsm, hydrophobic (i.e., untreated), polypropylene Spunbond-Spunbond-Spunbond (SSS) provided by Fitesa, Simpsonville, S.C. Solutions of SPI (e.g., Clarisoy 100®) were mixed at specified temperatures ranging from 22° C. to 80° C. The pH of the SPI solutions was not adjusted in these experiments. Solution pH values ranged from 2.3 to 2.9. A temperature of 22° C. was defined as room temperature, although in practice this could vary from about 15° C. to 30° C. The nonwoven was finished or treated with solutions of Clarisoy 100™ at specified temperatures ranging from 22° C. to 70° C. using a laboratory-scale padder. Samples were prepared using a two-stage dip-and-nip process to ensure uniform wetting of the nonwoven.

Solutions at the specified concentrations were made in 1500 ml to 3000 ml batches with tap water of medium hardness. Clarisoy 100® powder was slowly added to vigorously-stirred water that was held at the specified mixing temperature using a thermocouple-equipped hotplate with temperature control. After dispersing the powder in the heated water, mixing speed was reduced and maintained for 30 minutes. The solution became clear after 15 to 20 minutes of mixing. About half-way through the mixing step, 0.04% n-butanol was added to reduce foaming. In some embodiments, n-butanol is not necessary. A biobutanol such as Butamax®, which is produced from renewable resources, can optionally be used to reduce foaming. It is not necessary to use butanol when mixing under less vigorous conditions. Butanol did not have a significant effect on the surface tension of the solution. A 0.04% solution (i.e. 0.0054 M) of n-butanol would reduce the surface tension of water from a value of 72 mN/m only to about 62 mN/m. After mixing at the specified temperature, the solution was allowed to cool until reaching a specified treatment temperature. Samples were treated ±5° C. of a target treatment temperature.

The laboratory padder had two rubber-coated, vertical, 8 in. diameter rolls. Sufficient nip pressure was applied to target a wet pick up on the nonwoven in the range of 1.0 g. of solution/g. of nonwoven. Each 430 mm×430 mm section of nonwoven was immersed in a volume of about 1500 ml of solution at a specified treatment temperature before being calendared between the padder rolls. A two-stage dip-and-nip process was used to treat the nonwoven. Solution was not absorbed uniformly on the hydrophobic nonwoven after the first dip-and-nip cycle. Immediately after the first cycle, the nonwoven sample was re-immersed in the solution and calendared or nipped a second time. This two-stage dip-and-nip process produced a uniformly wet nonwoven and helped to distribute the dissolved solid uniformly over the fiber surfaces. The wet weight of the sample was recorded to determine wet pick-up of solution before hanging the sample in an oven at 107° C. for 15 min. to dry.

Drop values in FIG. 3 were measured using a 4-Hole Drop Test to provide a measure of the hydrophilicity of the treated nonwoven. Solids add-on was calculated from the solution concentration and the wet pick-up of solution on the nonwoven (expressed as g. of solution per g. of nonwoven). Average wet pick-up was calculated from the wet and dry weights of each of three handsheets as they were treated. The pooled standard deviation for wet-pick was 0.07 g/g. In the 4-Hole Drop Test a plastic plate with dimensions of 75 mm×75 mm×13 mm with four evenly spaced holes each of 15 mm diameter was placed on a sample of nonwoven which was resting on one piece of Whatman No. 4 filter paper (90 mm diameter). Using an eye dropper, four drops of tap water were dropped into one hole from a height equal to the thickness of the plastic plate. A Drop Value of 2, 1, or 0 was assigned according to how quickly the drop penetrated the nonwoven and was absorbed by the filter paper. A Drop Value of 2 was used to indicate that the liquid was spontaneously absorbed by the nonwoven within five seconds. A Drop Value of 1 indicated that the liquid was absorbed when the assembly of filter paper, nonwoven sample, and plastic plate was softly shaken after five seconds. A Drop Value of 0 indicated that the liquid was not absorbed. Average Drop Values were calculated from the average values obtained from each of four holes on four samples of nonwoven for a total of 16 measurements.

An untreated, hydrophobic nonwoven had average Drop Values in the range of 0 to 0.5. Drop Values of 2.0 were measured for hydrophilic SSS and Spunbond-Meltblown-Spunbond (SMS) nonwoven topsheets that had been treated with conventional finishes. An average Drop Value of greater than about 1.2 provided adequate hydrophilicity for liquid acquisition in an absorbent product. Drop Values less than 1.2 are shaded in FIG. 3. FIG. 3 shows that average Drop Values greater than 1.2 were achieved for solids add-on greater than 0.5% (or 0.005 g. of solids per g. of nonwoven) when the solution mixing temperature was equal to or greater than about 50° C. to 70° C. Drop Values were not affected by the application temperature of the solution, i.e. Drop Values greater than 1.2 were achieved when a nonwoven was treated with a solution at ambient temperature, or about 22° C., as long as that solution was mixed at a temperature equal to or greater than 50° C. The pooled standard deviation for the average Drop Values was 0.9.

Figure 4:
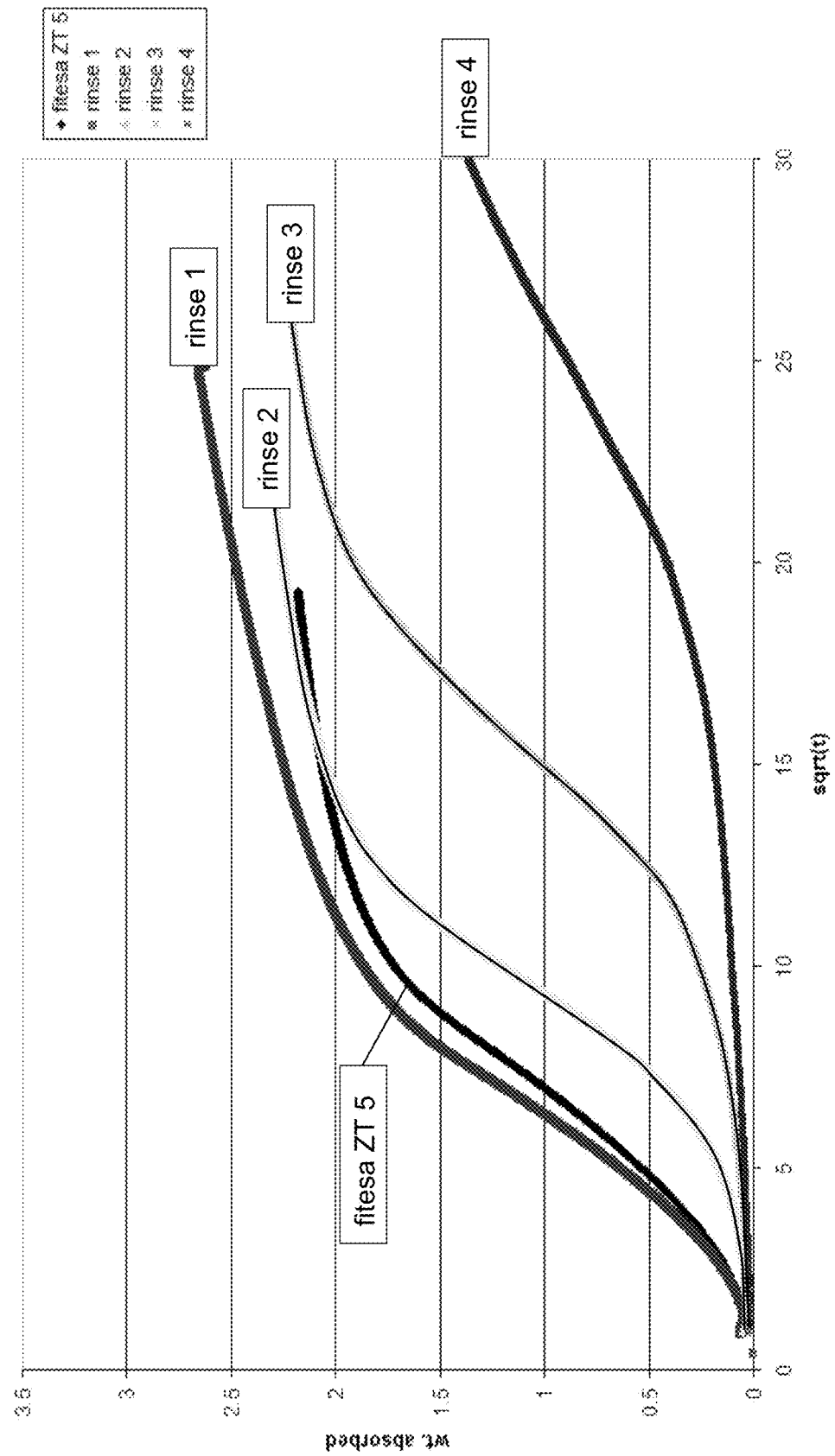
FIGS. 4-5 depicts absorbance versus the square root of time for rinse tests for one embodiment of the present sheets.

III. Wettability of Prototype Nonwovens Using Gravimetric Absorbent Test System Samples were produced for testing on a Gravimetric Absorbency Test System (GATS) to characterize the absorption of saline by the nonwoven over successive absorption cycles. The GATS test was used to assess the durability of the finish to multiple doses of saline solution. After each test, the nonwoven was removed from the apparatus and rinsed by immersion in 100 ml of 0.9% saline solution at room temperature for 1 minute, then blotted dry with a paper towel. The sample was immediately retested after each rinse. FIG. 4 shows the weight (g) of saline absorbed by three layers of nonwoven as a function of the square root of time ($sec^{0.5}$). The liquid was absorbed through a single aperture with the nonwoven sample supported by a finned plate. The finned plate reduced the amount of spurious liquid that could be absorbed between the nonwoven sample and the plate. Results in FIG. 4 were obtained using a commercial 12.5 gsm spunbond nonwoven that had been treated with a commercially-available, proprietary, semi-durable finish.

As shown in FIG. 4, liquid was absorbed more slowly after each of the four rinses. This was the expected result for wetting of a nonwoven that had a semi-durable finish. Note, however, that the induction time for absorption increased after each of the first three rinses while the actual rate of absorption after the induction period remained fairly constant. The induction time for wetting after the fourth rinse was very long, greater than 300 sec, and the rate of absorption after the onset of wetting much decreased.

Figure 5:
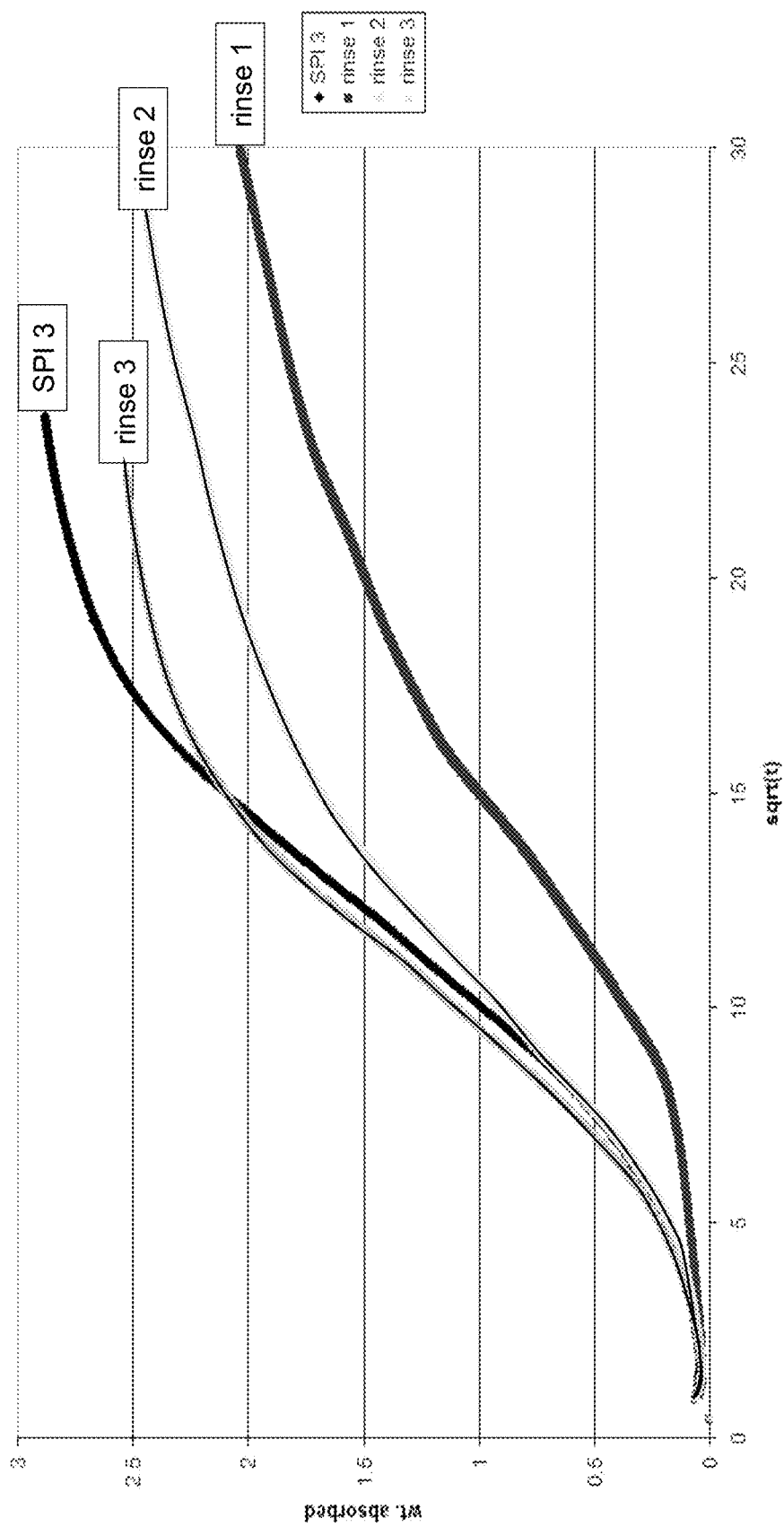

As shown in FIG. 5, a nonwoven with an SPI add on of 0.006 g. SPI/g. nonwoven showed much different behavior in this test. This nonwoven was finished on a pilot line described in Section V below. Liquid absorption of the unrinsed nonwoven with the SPI finish was comparable to that of the commercially available nonwoven with a conventional synthetic surfactant finish. After the first rinse there was a clear increase in the induction time of wetting and a modest decrease in the rate of wetting after the induction period, compared to the unrinsed sample. However, in contrast to the nonwoven with the commercially available synthetic surfactant finish, liquid absorption, performance of the nonwoven with a synthetic surfactant-free SPI finish improved after both the second and third rinses. Performance after the third rinse was typically as good or better than that of an unrinsed sample. This was an unexpected result, but can be explained by a finish that was extremely durable and improved as it hydrated during use.

IV. Spreading of SPI Solution within a Nonwoven Using a Calendar Nip

As shown in Section V below, a high-surface-tension saline solution (i.e. synthetic urine) will spread on and be imbibed by a polypropylene nonwoven that has been treated with a hydrophilic finish comprised of SPI. However, a high-surface-tension SPI solution will not readily spread on a hydrophobic polypropylene nonwoven. The nonwoven can be treated by immersing it in a solution of SPI and forcibly removing entrained air to ensure intimate contact between solution and nonwoven fibers. Once the solution comes in contact with the hydrophobic polypropylene fiber of the nonwoven, the protein adsorbs on the fiber surface and renders the nonwoven more hydrophilic, but the protein cannot adsorb to fiber in areas of the nonwoven that solution cannot spread.

Water with a surface tension of 72.8 mN/m does not spread on a low-surface-energy solid like polypropylene. Conventional nonwoven finishes that are in widespread use today are comprised of synthetic surfactants that lower the surface tension of water to a range of about 30-37 mN/m (see Table 1 below). These surfactant solutions of low surface tension spread on polypropylene fibers and provide a uniform distribution of surfactant finish upon drying. A 0.1% solids solution of Clarisoy® 100 SPI had a surface tension of 64 mN/m. This solution will not readily spread in a polypropylene nonwoven. Classes of materials that can be used to make a synthetic surfactant-free nonwoven finish described in this invention are hydrophilic, but solutions of these materials do not reduce the surface tension of water below 49 mN/m. These solutions are not spontaneously imbibed by hydrophobic nonwovens, and require special processing to uniformly distribute the finish throughout the nonwoven structure.

The surface tensions of solutions of Clarisoy® 100 SPI at concentrations in the range of 0.4%-1.2% solids were in the range of 49-68 mN/m at 22° C. The mean value was 58±9.9 mN/m. At these concentrations the surface tension was independent of solution concentration. Surface tension was measured using a method of capillary rise. Capillary rise was measured after raising and lowering the liquid in the capillary and measuring the values at equilibrium after 10 min.

TABLE 1

Surface Tensions of Liquids and Solutions

| Liquid | Surface Tension (mN/m) |
|---|---|
| Water | 72 |
| SPI solution (0.4%-1.2%) | 49-68 |
| 0.1% 7 B Soy Flour | 61 |
| Silastol 163 (0.4%-6%) | 35-37 |
| Silastol PHP 26 (0.4%) | 30 |
| Stantex S6757 (0.4%-6%) | 31-36 |
| 0.1% Triton X-100 | 33 |
| Isopropyl alcohol | 22 |

The Silastol and Stantex materials in Table 1 are surface finishes comprised of proprietary mixtures of synthetic surfactants that are used to render polypropylene spunbond nonwoven hydrophilic. Silastol 163 is a silicone-free, anionic finish for the production of durable hydrophilic polyolefin nonwovens, especially topsheets. Silastol PHP 26 is a cationic/amphoteric finish for the production of durable hydrophilic polyolefin staple and spunbond fibers suitable for topsheet. Stantex S 6757 is durable hydrophilic finish for polypropylene spunbond materials, especially for hygienic applications. These surfactants are often applied to nonwoven using solution concentrations in the range of 6%. At solids in the range of 0.4%-6%, solutions of these materials had a surface tension in the range of 31-37 mN/m. The low surface tension of these solutions promotes wetting of the hydrophobic polypropylene nonwoven and enables the nonwoven to spontaneously imbibe the surfactant solution.

To achieve spreading and contact between an SPI solution and a hydrophobic nonwoven, the nonwoven was immersed in an SPI solution and calendared to eliminate entrained air and promote intimate contact, even for a short period, between nonwoven fiber and solution. A laboratory calendar with an adjustable nip was used simulate what could be achieved using a flooded nip or size press on a commercial production line. Table 2 shows how the solution concentration of SPI was increased to compensate for a reduced wet pick up of solution after calendaring. A critical nip dimension of about 0.150 (in arbitrary units) was required to achieve uniform wetting of the nonwoven in this calendar. There was a large reduction in wet pick up for calendared nonwoven, but no meaningful change in wet pick up for small changes in nip dimension near the critical value.

TABLE 2

Properties of Certain of Methods of Making the Present Sheets

| Dry Wt. of Nonwoven Sample | Solution Concentration (g. SPI/g. NW) | Nip Dimension | Wet Pick Up (g. soln/g. NW) | SPI Add On (g. SPI/g. NW) |
|---|---|---|---|---|
| 0.08 | 0.001 | None | 6.0 | 0.006 |
| 0.08 | 0.001 | 0.200 | 2.3 | 0.002 |
| 0.08 | 0.002 | None | 6.4 | 0.013 |
| 0.08 | 0.002 | 0.200 | 2.8 | 0.006 |
| 0.08 | 0.002 | 0.150 | 3.0 | 0.006 |
| 0.08 | 0.002 | 0.125 | 3.0 | 0.006 |
| 0.08 | 0.004 | 0.125 | 3.0 | 0.012 |

Runoff tests were used to assess the ability of a stream of liquid to penetrate a topsheet nonwoven and to be absorbed by an absorbent core before the liquid could run over the surface of the topsheet nonwoven to the end or side of an absorbent article. Two runoff tests were used in this work. One test utilized a model absorbent core and the other used absorbent cores from actual baby diapers. In this section the test with the model absorbent core, as described in Section X.C below, was used. The other test will be discussed in a later section to evaluate the properties of nonwoven prototypes that had been made on a pilot line and evaluated on baby diapers.

As shown in FIG. 6, performance of 12-13 gsm spunbond nonwovens finished with a synthetic surfactant-free topsheet finish at 0.006 g. SPI/g. nonwoven was compared to that obtained for a commercially available nonwoven finished with a semi-durable synthetic surfactant. The data clearly show comparable performance for the synthetic surfactant-free topsheet finish. There was a modest reduction or improvement in Liquid Runoff for the nonwoven with the surfactant-free finish, even though the liquid travel may have been somewhat greater than that measured for the commercial nonwoven topsheet with a semi-durable surfactant finish.

V. Synthetic Surfactant-Free Nonwoven Finishes Applied on a Pilot Line

A high-surface-tension aqueous solution of SPI will not readily spread on a hydrophobic polypropylene nonwoven. In earlier sections it has been shown that lab prototypes can be prepared successfully by immersing a sample in a solution and calendaring it to evenly distribute solution throughout the nonwoven. A pilot line with a flooded nip size press at North Carolina State University was used to validate this approach. Identification of a process that does not require spontaneous spreading of the aqueous synthetic surfactant-free solution on the hydrophobic, untreated nonwoven was considered to be important for commercial use of at least some of the present embodiments. The flooded nip on the pilot line was set up and adjusted to achieve uniform wetting of the web in machine- and cross-directions. The nonwoven was successfully processed using a steel on rubber roll configuration where the Durometer Hardness of the rubber roll had a value of 72. Roll pressure was adjusted until the wet pick up of the solution on nonwoven was qualitatively uniform in appearance and touch in both MD and CD directions. Variability in wet pick up was checked by weighing samples that had been cut from the web. After adjustment, wet pick up on nonwoven varied less than 10%. A uniform wet pick up of solution could not be achieved using a harder rubber roll with a Durometer Hardness of 90.

Preparation of SPI solution for pilot line runs was done as closely as possible to lab protocol described above. SPI powder was mixed with distilled water (<10μ mho conductivity) in a five gallon pail using a high-shear mixer at 6000-7000 rpm for 15 minutes at room temperature. The solution was adjusted from its natural pH of 2.7-3.0 to a pH of 8.0±0.2 before being placed in a steam jacketed reservoir on the pilot line. It took about 15 minutes for the solution to reach temperature in the pilot line. The solution was maintained at a temperature of about 90° C. in the reservoir to ensure an application temperature of 80° C. in the flooded nip. Wet pick up of solution on the pilot line was less than that achieved using the laboratory calendar. Prototypes made in the lab had a wet pick up of about 3 g. solution/g. nonwoven, but only about 1 g. solution/g. nonwoven remained on the nonwoven on the pilot line after the roll pressure in the flooded nip had been increased to achieve uniform wetting. Solution concentration was adjusted upward during the pilot line trials to achieve a target add on of SPI in the range of 0.006-0.008 g. SPI/g. nonwoven.

Steam can rolls were maintained at 110° C. on the pilot line to dry the nonwoven at a line speed of 30 feet/minute. Prototypes made on the pilot line are listed in Table 3 below.

TABLE 3

Pilot Line Prototypes

| Prototype No. | Base Nonwoven | Solution Conc. (g. SPI/g. soln) | Wet Pick Up (g. soln/g. NW) | SPI Add On (g. SPI/g. NW) |
|---|---|---|---|---|
| 1 | 12 gsm SSS | 0.0025 | 1.0 | 0.003 |
| 2 |  | 0.0050 | 1.2 | 0.006 |
| 3 | 15 gsm SMS | 0.0025 | 1.1 | 0.003 |
| 4 |  | 0.0050 | 1.0 | 0.005 |
| 5 |  | 0.0100 | 0.8 | 0.008 |

As described below, several of these prototypes were incorporated into baby diapers for testing, and certain characteristics and test results are summarized in FIG. 7. The testing methods are described in the "Experimental Methods" section below.

A. Example No. 1

This example shows the lab performance of a leading private label baby diaper (Size 4) reconstructed with a 12 gsm SSS spunbond nonwoven topsheet that had been treated with a synthetic surfactant-free SPI finish (Prototype No. 2 above, with 0.006 g. SPI/g. nonwoven). The topsheet of the commercially available diaper was carefully removed by gentle heating with a forced air hair dryer and replaced with the prototype topsheet. All other materials, including the 60 gsm acquisition/distribution layer used on the commercial diaper remained the same. To minimize the effect of diaper reconstruction on interpretation of test results, especially for runoff tests, the topsheet of the control or commercial diaper was also removed and then replaced in its original position. The topsheet of the commercial diaper comprised a 15 gsm nonwoven.

A diaper containing an unfinished hydrophobic spunbond topsheet was included for reference in FIG. 7. This hydrophobic topsheet generated poorer performance in third and fourth dose liquid acquisition time (ACQ3 & ACQ4) and poorer performance in side leakage in this test. Higher side leakage in the ACQ(uistion)/REW(etting) test was related to the very high runoff volumes exhibited by the hydrophobic nonwoven. In comparison, performance of the diaper that contained the nonwoven topsheet that had been treated with the synthetic surfactant-free finish was comparable to that of the diaper containing the original, synthetic surfactant-finished topsheet. The synthetic surfactant-free, hydrophilic SPI finish had imparted useful properties to the initially hydrophobic topsheet nonwoven. In the Anarewet Test, there was a notable advantage in side leakage for the diaper containing the synthetic surfactant-free topsheet. Runoff improved after each successive dose for the diaper that contained the synthetic surfactant-free topsheet. Mannequin leakage, expressed as absorption before leakage (ABL) was significantly improved from 206 g. to 250 G. for the diaper containing a topsheet nonwoven with a synthetic surfactant-free finish.

B. Example No. 2

This example shows the lab performance of a leading private label baby diaper (Size 4) reconstructed with a 15 gsm SMS nonwoven topsheet that had been treated with a synthetic surfactant-free SPI finish (0.008 g. SPI/g. nonwoven). The synthetic surfactant-free topsheet used with this diaper was Prototype No. 5 that was made in the pilot line trial described above. The topsheet of the commercially available diaper was carefully removed by gentle heating with a forced air hair dryer and replaced with the prototype topsheet. All other materials, including the 60 gsm acquisition/distribution layer used on the commercial diaper remained the same. To minimize the effect of diaper reconstruction on interpretation of test results, especially for runoff tests, the topsheet of the reference diaper was also removed and then replaced in its original position.

A diaper containing an unfinished hydrophobic SMS topsheet was included for reference in FIG. 7. The diaper containing the SMS topsheet with the synthetic surfactant-free finish showed comparable performance to the commercially available diaper, but provided a significant advantage in side leakage in the Anarewet Test. Runoff also improved after each successive dose for the diaper that contained the synthetic surfactant-free topsheet. The synthetic surfactant-free SPI treatment had imparted an effective hydrophilic finish to the topsheet nonwoven.

Further optimization of the performance of topsheet and acquisition/distribution layer (ADL) nonwovens finished with SPI, as well as other materials, can proceed using solution concentration, solution pH, solution mixing temperature, nonwoven treatment temperature, calendaring to promote liquid spreading, and drying temperature. The invention can be extended to include other hydrophilic, but non-surface active, materials. Examples of these will be discussed in a later section.

VI. Additional Examples

Examples 3-6 show liquid acquisition and rewet performance of diapers that had been reconstructed with topsheet nonwoven that had been finished using a laboratory padder as described in the earlier section "Hydrophilicity as a Function of Mixing and Application Temperatures of Solutions." A reconstructed diaper is a machine-made diaper that has had its original topsheet nonwoven dissected and replaced with test material. Control diapers for this experiment had the original topsheet also dissected and replaced to reproduce any differences in liquid communication within the diaper that may have been introduced by the reconstruction process. Size Large diapers from a leading private label producer were used to evaluate the topsheets. The absorbent core of the diaper was comprised of 45% fluff and 55% SAP. There was about 11.5 g. of SAP in the absorbent core of the diaper. A partial core length, 50 gsm through-air-bonded acquisition layer was used between the topsheet and the core. Examples 3-6 provide results from the Liquid Acquisition and Rewet (ACQ/REW) Test for diapers reconstructed with SSS topsheet nonwovens that had been finished using various combinations of solution concentrations of SPI, types of SPI, SPI add-on levels, solution mixing temperatures, and solution application temperatures. The pH of the SPI solutions used to make these samples was not adjusted. Their natural pH was in the range of 2.2-2.9. The Drop Values for the topsheet nonwovens used in these examples ranged from 1.4-2.0. Example 7 provides a comprehensive assessment of a machine-made diaper that had been produced with a machine-made SSS topsheet nonwoven finished with SPI.

The SPI-finished topsheet nonwoven in Example 3 (1.2% Clarisoy® 100 solution mixed at 80° C. and applied at 22°

C.), as indicated in Table 4, as evaluated in a lab-reconstructed diaper. Results of testing of Example 3 are shown in FIG. 8.

TABLE 4

Properties of Example 3
Clarisoy 100 ®

| Solution Concentration (%) | SPI Add-On (g solids/g nonwoven × 100%) | Mix Temperature (° C.) | Application Temperature (° C.) | 4-Hole Drop Value |
|---|---|---|---|---|
| 1.2% | 2.0% | 80° C. | 22° C. | 2.0 |

Example 4 included a lab-made SPI-finished nonwoven evaluated in a lab-reconstructed diaper (1.2% Clarisoy® 150 solution mixed at 80° C. and applied at 22° C.), as indicated in Table 5. Results of testing of Example 4 are shown in FIG. 9.

TABLE 5

Properties of Example 4
Clarisoy 150 ®

| Solution Concentration (%) | SPI Add-On (g solids/g nonwoven × 100%) | Mix Temperature (° C.) | Application Temperature (° C.) | 4-Hole Drop Value |
|---|---|---|---|---|
| 1.2% | 2.0% | 80° C. | 22° C. | 2.0 |

Example 5 included a lab-made SPI-finished nonwoven evaluated in a lab-reconstructed diaper (0.8% Clarisoy® 100 solution mixed at 80° C. and applied at 50° C.), as indicated in Table 6. Results of testing of Example 5 are shown in FIG. 10.

TABLE 6

Properties of Example 5
Clarisoy 100 ®

| Solution Concentration (%) | SPI Add-On (g solids/g nonwoven × 100%) | Mix Temperature (° C.) | Application Temperature (° C.) | 4-Hole Drop Value |
|---|---|---|---|---|
| 0.8% | 1.1% | 80° C. | 50° C. | 2.0 |

Example 6 included a lab-made SPI-finished nonwoven evaluated in a lab-reconstructed diaper (0.8% Clarisoy® 100 solution mixed at 50° C. and applied at 22° C.), as indicated in Table 7. Results of testing of Example 6 are shown in FIG. 11.

TABLE 7

Properties of Example 6
Clarisoy 100 ®

| Solution Concentration (%) | SPI Add-On (g solids/g nonwoven × 100%) | Mix Temperature (° C.) | Application Temperature (° C.) | 4-Hole Drop Value |
|---|---|---|---|---|
| 0.8% | 0.7% | 50° C. | 22° C. | 1.4 |

Examples 3-6 show that the SPI-treated nonwovens are suitable for use in an absorbent product and can provide a meaningful improvement in Surface Wetness over a conventional nonwoven finished with synthetic surfactant. Saline was maintained at 22° C. for tests in Examples 3-6. Overall, the diapers containing the SPI-treated nonwovens had somewhat lower (i.e., better) liquid acquisition times and higher (i.e., poorer) rewet values after the first dose. This behavior is consistent with SPI providing a more durable hydrophilic finish than synthetic surfactant. Synthetic surfactant used in the conventional finish is washed from the nonwoven in use, and the nonwoven becomes less hydrophilic after each dose. This results in higher acquisition times and lower rewet on subsequent doses of liquid compared to the performance of the diaper made with the SPI-treated nonwoven. The reduction in liquid acquisition times for diapers with the SPI-treated nonwoven topsheets were not statistically significant at p=0.05, but consistent and directional with p values generally less than 0.20. There were meaningful reductions in Surface Wetness for diapers made with the SPI-treated nonwoven topsheets. For example, after the fourth dose, Surface Wetness for the diapers with the SPI-treated topsheets ranged from 0.000-0.027 g. compared to a value of 0.050 g. for the diaper with the conventional topsheet. Surface Wetness is a measure of small amounts of saline that can remain trapped between a wearer's skin and the nonwoven on the surface of the product. It is important because synthetic surfactant from a nondurable nonwoven finish can dissolve in urine and contact skin. The presence of synthetic surfactant on skin may be associated with skin irritation and transient erythema, as well as an increase in the permeability of the skin to any irritant that may be present. Side leakage for diapers with the SPI-treated topsheets was less than for diapers with the conventional, synthetic surfactant-treated topsheet.

Example 7 included a machine-made SPI-treated nonwoven evaluated in a machine-made diaper (solution mixed at 80° C. and applied at 65° C.), as indicated in Table 8. Results of testing of Example 7 are shown in FIG. 12.

TABLE 8

Properties of Example 7
Clarisoy 100 ®

| Solution Concentration (%) | SPI Add-On (g solids/g nonwoven × 100%) | Mix Temperature (° C.) | Application Temperature (° C.) | 4-Hole Drop Value |
|---|---|---|---|---|
| 1.4% | 0.6% | 80° C. | 65° C. | 2.0 |

A commercial-scale textile finishing line at TSG Finishing (Hickory, N.C.) was used to produce 5,000 lineal meters of a SPI-treated nonwoven for making prototype diapers on a commercial-scale converting machine. The base nonwoven was a hydrophobic (i.e., unfinished), 12.5 gsm Fitesa SSS spunbond nonwoven. The padder process was modified to finish the topsheet using a two-stage dip and nip process at 50 yd./min. with a solution of Clarisoy 100 maintained at 60°-70° C. The solution was prepared at 1.2 wt. % of Clarisoy® 100 and 0.04 wt. % of n-butanol, however due to evaporative losses during the trial run, the average solution concentration was about 1.4%. Tap water was heated to a temperature of 80° C. before adding the Clarisoy 100 and mixing for 30 min. The solution was used at its natural pH in the range of 2.2-2.9. Solids add-on calculated from wet pick-up of solution on the nonwoven was 0.006 g. solids per g. of nonwoven. The nonwoven was dried on a tenter frame in an air impingement oven at 225° F. Rolls of the SPI-treated nonwoven were used to make infant diapers on a commercial-scale converting machine at Domtar Personal Care in Delaware, Ohio. Size Large diapers used for this evaluation were made with a 45% fluff/55% superabsorbent polymer (SAP) absorbent core comprised of 11.5 g. of SAP. A 50 gsm acquisition/distribution layer (Shalag Nonwovens, Oxford, N.C.) of through-air-bonded synthetic fiber was placed in the diaper between the absorbent core and topsheet. Diapers were made with both a conventional 13.5 gsm SMS topsheet nonwoven and at 12.5 gsm SPI-treated topsheet nonwoven, and were evaluated using 4-Hole Drop, Conventional Liquid Acquisition/Rewet, Anarewet Liquid Acquisition, Liquid Runoff, and Mannequin Leakage Tests.

This SPI-treated topsheet nonwoven was uniformly wettable and suitable for use as a topsheet nonwoven in an absorbent product. Drop values obtained using the 4-Hole Drop Test were 2.0±0.01 for SPI-treated nonwoven produced both at the beginning and at the end of the trial run.

Values of Liquid Acquisition and Rewet for diapers made with a conventional nonwoven topsheet and the SPI-treated topsheet were generally comparable (FIG. 12). Tests were run using saline solutions at 22° C. and 37° C. There were statistically significant (i.e., $p<0.05$) improvements in liquid acquisition times at 22° C. for all doses for the diaper made with the SPI-treated nonwoven. At 37° C., due to higher variability in the acquisition times, there was only a directional improvement in fourth dose acquisition time with $p=0.14$. There were directionally poor Rewet values after the third and fourth doses for the SPI-treated nonwoven. These increases in Rewet were small and not statistically significant. As noted in earlier testing, Surface Wetness and Side Leakage were better for the diaper made with the SPI-treated topsheet.

Similarly, there were directional indications of improved Anarewet Liquid Acquisition times at both 22° C. and 37° C. for the SPI-treated nonwoven that were not statistically significant (FIG. 13). The rate of liquid acquisition in the Anarewet Test depends more on demand absorbency than it does in a conventional ACQ/REW liquid acquisition test. Acquisition rate in the Anarewet Test would be expected to be more sensitive to the hydrophilicity and durability of the topsheet finish. For saline solutions at 22° C., there were: statistically significant ($p<0.05$) reductions in Liquid Acquisition time at all doses for the diaper with the SPI-treated nonwoven, directionally higher Rewet after the 4th dose for the diaper with the SPI-treated nonwoven but not statistically significant ($p=0.152$), comparable surface wetness, and higher side leakage for the diaper with conventional topsheet. For saline solutions at 37° C., there were: no statistically significant differences in Liquid Acquisition time, directionally lower 4th dose Liquid Acquisition time for diaper with the SPI-treated nonwoven ($p=0.138$), directionally higher Rewet after 4th dose for the diaper with the SPI-treated nonwoven but not statistically significant ($p=0.402$), comparable Surface Wetness, and higher Side Leakage for the diaper with conventional topsheet.

Liquid Run-Off performance for the diaper containing the SPI-treated nonwoven was significantly better than that of the control diaper that contained the conventional nonwoven (FIG. 14). The saline in the Liquid Run-Off Test was adjusted to a surface tension of 60 mN/m with isopropyl alcohol and maintained at 37° C. After the first dose, there was a meaningful reduction in Run-Off for the diapers containing the SPI-treated nonwoven. Reductions in liquid run-off and liquid acquisition time over multiple doses are the result of a more durable hydrophilic nonwoven finish imparted by the SPI treatment.

Reductions in liquid run-off would be expected to reduce urine leakage in absorbent products. Evidence of reduced urine leakage has been demonstrated in an Infant Mannequin Leakage Test. There was a statistically significant ($p=0.015$) increase (i.e., improvement) in Absorption Before Leakage (ABL) of the infant diapers made with the SPI-treated nonwoven. ABL values of 226 g. and 200 g. were obtained for the diapers with the SPI-treated and conventional nonwoven topsheets, respectively. ABL for an absorbent product can generally be increased by increasing core capacity, as well as by improving containment related to product design and fit, however it was an unexpected result of this invention to measure a 13% increase in ABL with use of an SPI-treated topsheet nonwoven alone.

VII. Preservatives for SPI Solutions

Soy protein can provide nutrients for yeast and bacterial growth when sufficient moisture is present. There is little concern for microbial growth on an SFT-finished nonwoven under normal conditions of storage and use. When aqueous solutions of soy protein are prepared and stored prior to manufacture of an SFT nonwoven it may be necessary to add a preservative to the solution to provide adequate shelf life. Peracetic acid can be used to sterilize the solution, and conventional preservatives such as sulfites, benzoic acid and sodium benzoates can be effective. Preservatives such as ascorbic acid, sorbic acid, Natamycin, taurine, aspartame, nisin, polyhexamethylene biguanide hydrochloride, and elemental silver may also be effective. It is important to assure that the preservative does not impair the hydrophilicity or durability of the SFT nonwoven finish. Plantservative WSr (BioOrganic Concepts, Santa Fe Springs, Calif.), derived from Japanese honeysuckle, and Nutrabiol T30 WD (Food Ingredient Solutions LLC, Teterboro, N.J.), a tocopherol derivative, maintain 4-Hole Drop values >1.2 for nonwovens with SPI add-on in the range of 0.02-0.020 g. SPI/g. of nonwoven when the preservatives are incorporated into the SPI finish such that the ratio of preservative to SPI does not exceed a value of about 0.08 to 1, or the preservative amounts to no more than about 8% of SPI on the nonwoven.

VIII. Other Hydrophilic, Non-Surface Active Materials for Nonwoven Finishes

A. Examples of Other Soy Materials

ProFam® 974 is another soy protein isolate. Arcon S and Arcon SM are soy protein concentrates with better water dispersibility than soy protein isolates. 7B Soy Flour, Bakers Soy Flour, and Bakers Soy Flour are defatted soy flours. In addition to these materials produced by ADM, Cargill Incorporated produces Prolia defatted soy flours.

Solutions of other soy materials were made using 0.001 g. powder/g. solution and mixed at 80° C. for 60 minutes. All of these materials were more easily dispersed in water than Clarisoy 100. No pH adjustments were made. The pH of the solutions are shown in FIG. 15. Hydrophobic spunbond was treated by immersion in the solution at 80° C. for 30 seconds and dried in an oven at 120° C. A drop test discussed in a previous section was used to assess the hydrophilicity of the treated nonwovens, results of which are shown in FIG. 15. As indicated, all of the nonwovens treated with the soy materials performed as well as the commercially available topsheet made with a semi-durable surfactant finish. There was some evidence after a warm tap water rinse that these synthetic surfactant-free soy-finishes were more durable than the commercial surfactant finish. The good performance of these other soy materials suggests that many other natural and synthetic materials may fall within the teaching of this invention.

B. Hydrolyzed Proteins and Gelatin

Various plant- and animal-derived biopolymers may provide additional examples for the present finishes. For example, hydrolyzed collagen, hydrolyzed albumen, hydrolyzed barley protein, hydrolyzed casein, hydrolyzed cottonseed protein, hydrolyzed gelatin, hydrolyzed hemp seed protein, hydrolyzed whey protein, casein, hydrolyzed silk, glutelin proteins, silk sericin, gum arabic, bovine serum albumin, and various vegetable proteins. Of particular interest are the Peazazz® pea protein and Supertein® canola protein isolates produced by Burcon NutraScience Corporation and zein produced by Flo Chemical Corporation.

C. Polyvinylpyrrolidone (PVP)

PVP is a water-soluble, nonionic polymer that adheres to a variety of substrates. BASF (Kollidon®), Harke Group and International Specialty Products (ISP) produce PVP polymers in several viscosity grades, ranging from low to high molecular weight. PVP is mainly used as a binder in wet granulation and hair spray products. Copolymers of vinyl pyrrolidone and vinyl acetate are also commercially available. PVP will crosslink in air at 150° C. and become insoluble in water. Crosslinking would impart exceptional durability to a nonwoven finish comprised of PVP. These properties suggest that PVP would function particularly well as a hydrophilic nonwoven finish, as well as an inert scaffold for the incorporation of microsilver or skin wellness ingredients.

D. Other Hydrophilic Polymers

Hydrophilic, water-soluble polymers like carboxymethyl cellulose (and other cellulosic polymer derivatives), starches, polyvinyl alcohol, and polyethylene and polypropylene glycols for providing less durable nonwoven finishes. Many polysaccharides may also provide examples of this invention.

IX. Durable, Synthetic Surfactant-Free Finishes as Carrier for Skin Wellness Ingredients The durable, synthetic surfactant-free finishes described in this invention can also be used as a carrier or scaffold for incorporation of skin wellness ingredients in a nonwoven finish for application in absorbent products. The durability of the finish can be adjusted to accommodate the desired rate of delivery of any particular active ingredient to wet skin. Examples of skin wellness ingredients include anti-infective agents such as silver powder (e.g., MicroSilver), silver sulfadiazine, povidone iodine, and PVP-stabilized peroxides; anti-viral agents such as citric acid, copper oxide, and Zn salts; anti-microbial (e.g., plantservative) and, various skin-rejuvenation ingredients widely used in the cosmetic industry. A synthetic-surfactant-free SPI finish provides a novel, skin-friendly vehicle for incorporating biopolymers such as 2-methacryloyloxyethyl phosphorylcholine (MPC) and its derivatives into a nonwoven finish to impart bioinert properties and form a hydration shell of water around nonwoven fibers.

X. Experimental Methods

A. Liquid Acquisition and Rewet (ACQ/REW)

A conventional liquid acquisition and rewet test was performed according to the following procedure. The liquid acquisition is the time in seconds for a section of core to absorb a known volume (usually 75 or 100 ml) of 0.9% saline through a 48 mm diameter dosing head. Products were equilibrated overnight and tested in a room maintained at 22° C. and 50% relative humidity (RH). The saline solution was used at a room temperature of 22° C. The dosing head was weighted and had a screen on one end to apply an even pressure of 0.5 pounds per square inch (psi) to the core at the point of liquid dosing. The remainder of the core was restrained under a 150 mm×300 mm plate that weighed 600 g. The dosing head extended through a hole drilled through the core restraining plate and was positioned over the center of the acquisition layer used on the absorbent core. A 75 ml dose was metered to the dosing head at a rate of approximately 20 ml/sec and the time to absorb the liquid was recorded as the acquisition time (±0.1 sec). After 30 minutes of equilibration, the restraining plate was removed, and a stack of ten filter papers (Whatman 4, 70 mm) were placed on the dosing area under a cylindrical brass weight of 60 mm diameter. The weight applied a pressure of 0.8 psi. After two minutes the weight was removed and rewet was determined from a difference in weight between the wet and dry filter papers (±0.01 g). The acquisition and rewet test was repeated for 4 doses.

Surface Wetness and Side Leakage were also determined in this test. Surface Wetness was determined when the restraining plate was removed from the core. A paper towel was used to collect liquid still attached to the plate after the plate had been removed from the core. A single paper towel was used to remove liquid from three to five plates used for replicate samples. The mass of the liquid from the plates was determined from a difference in weight between the wet and dry paper towel (±0.01 g.). An average Surface Wetness for each replicate was determined by dividing the total mass of liquid collected from the plates by the number of replicates. The steps were repeated for four doses of 75 ml of liquid.

Side leakage tests were also performed in conjunction with the Liquid Acquisition and Rewet testing. Side leakage can occur by liquid running off of the surface of the core, as well as by moving through the core itself and leaking from the side. In this test, a disposable absorbent bed pad was cut to a width that was 50 mm wider (i.e., 25 mm on each side) than the diaper and placed under the diaper at the beginning of the test. This mat was used to contain any test liquid that was not absorbed by the diaper core during the test. At the end of the test, the bed pad material was re-weighed to determine the amount of leakage that occurred during the test. Values of Side Leakage obtained for each replicate were combined to provide an average value of Side Leakage for the test.

B. ANAREWET Test

The Anarewet test was used to find acquisition times for products without forming a hydrostatic head over the dosing area. In particular, the Anarewet apparatus doses the liquid only when a product being tested can absorb it. A 75 ml dose of 0.9% saline solution at 22° C. was applied to the product at a pressure of 20 millibars (mb) and the acquisition or absorption time (without hydrostatic head) was measured.

C. Runoff Test Procedure for FIG. 6

This runoff test simulates the washing/rinsing off (or lack thereof) of surfactants or other nonwoven treatments which often occurs under subsequent insults of saline solution over the top of, or through, a nonwoven top-sheet. This run-off test was performed with an absorbent core and topsheet that were secured on a plexiglass plate that was inclined 20° above horizontal such that the liquid would flow laterally across the surface of the product. A tray was positioned under the lower end of the sample to collect runoff Six 75 ml doses of 0.9% saline at 22° C. were then applied at 420 ml/min at 5 minute intervals from a tube with its end disposed 1 cm above the core and dispensing liquid at an angle parallel to the incline of the product in a direction from the front toward the back of the product. For each dose, the saline that immediately ran off the topsheet (not leaking from the core over time) was collected in the tray and the change in weight measured.

D. Runoff Test Procedure for FIG. 14

This run-off test was performed with whole diapers. Diapers were secured on a plexiglass plate that was inclined 33° above horizontal, and oriented such that liquid from a nozzle would flow under gravity from the front to the back of the diaper. A nozzle was centered over the acquisition layer in the diaper in a vertical orientation 1 cm from the surface of the diaper. For each dose, the volumetric liquid flow rate was held constant at 420 ml/min for respective doses of 35, 70, and 105 ml. The diameter of the nozzle orifice was selected to provide a maximum liquid stream velocity of 200 cm/sec at a flow rate of 1200 ml/min. The test liquid was a 0.9% saline solution that had its surface tension reduced to 60 mN/m (at 22° C.) with isopropanol. The solution was heated such that the temperature of the solution at the nozzle exit was 35° C. After each dose, liquid that was not absorbed by the diaper core was collected at the base of the incline. Two additional doses at the same dose volume were administered at an interval of two minutes. Run-off was determined as a function of dose volume using dose volumes of 35, 70, and 105 ml per dose.

E. Mannequin Testing

For the mannequin testing, Large Size 4 diapers were constructed to include topsheets according to the present embodiments. These diapers were tested on a Size 4 prone Courtray mannequin diaper tester commercially available from SGS Courtray EURL, Douai, France, using the Courtray absorption before leakage (ABL) protocol provided with the apparatus.

The mannequin is made of a soft silicone rubber and has appropriate dimensions for a Large Size 4 infant. In this test a diaper was fitted to the mannequin and stressed until leakage with multiple doses of 0.9% saline test liquid supplied by Lab Chem Inc., Cat. No. 07933, which had a specification of 0.9% Wt./Vol. ±0.005% sodium chloride. Products were equilibrated overnight and tested in a room maintained at 22° C. and 50% relative humidity. The saline solution used was at a room temperature of 22° C. Absorption Before Leakage (ABL) was defined as the mass of liquid that the diaper absorbed (±0.01 g.) under conditions of the test before a leak occurred. Higher values of ABL=(Final Weight of Diaper after Leakage)−(Initial Dry Weight of Diaper) are preferred. The mannequin was provided with female and male dosing tubes. The male mode was used in all tests. The liquid was pumped to the mannequin at a rate of 7 ml/sec using a Masterflex L/S Digital Drive, Model No. HV-07523-80 and a Masterflex L/S Easy-Load II Pump Head, Model No. EW-77200-62. The mannequin was placed on a rectangular foam pad that had a waterproof cover. Leakage was detected visually on a sheet of tissue placed under the mannequin. Times were measured using a stopwatch ±1 sec.

General instructions for fitting a diaper on the mannequin follow. The diaper should be folded in the longitudinal direction forming a pouch, concave inward, between the legs of the mannequin. The standing gathers of the product need to come to rise while applying it to the mannequin, paying close attention to how they lie in the groin. Correct position is achieved when the standing gathers remain extended and surround the male adapter evenly. The outer leg elastics are folded outwardly in the crotch region so that the inner face of the product remains in contact with the skin of the mannequin. The tabs of the diaper are unfolded and put on smoothly. The diaper is spread flatly on front and backside to ensure an even fit. The diaper is then fixed in place with the tape tabs. The tabs should be centered on the landing zone. On a Size 4 Large diaper the ends of the tabs should nearly touch (1 mm ±0.5 mm) in the middle of the landing zone. The front and back ends of the diaper should remain at equal height on the torso of the mannequin. Small adjustments can be made to align the front and back ends of the diaper, if necessary. Differences in diaper dimensions can affect the tightness of fit of the diaper around the waist of the mannequin. In the testing described below, folded multi-layer cores were tested in commercially-available diaper chassis.

The protocol for liquid dosing of the product is given in the table below. An initial dose of 75 ml of liquid was delivered at t=0 with the mannequin lying on its belly. At t=4 min. the mannequin was turned on its back. At t=5 min. a dose of 25 ml was delivered with the mannequin lying on its back. At t=9 min. the mannequin was turned onto its belly, rotating the torso in the same direction as turned initially. At t=10 min. a dose of 75 ml was delivered with the mannequin lying on its belly. The mannequin remained on its belly for the remainder of the test and was dosed with 25 ml every 2 min. (e.g., t=12, 14, 16 min., etc.) until leakage occurred. Saline solution that leaks out of the diaper will be absorbed and spread by the tissue layer that covers the pad and will present a visible dark spot. After a leak occurred, the diaper was removed and weighed. The difference between the wet and initial dry weights of the diaper was defined as Absorption Before Leakage (ABL).

| Time (min) | Position | Dose No. | Dose Vol. (ml) |
|---|---|---|---|
| 0 | Belly | 1 | 75 |
| 4 | Back | — | — |
| 5 | Back | 2 | 25 |
| 9 | Belly | — | — |
| 10 | Belly | 3 | 75 |

After 10 min. the mannequin remains on its belly and is dosed with 25 ml every 2 min. until a leak occurs.

The diaper chassis used for making diapers containing the present topsheets was a commercially available, private label disposable diaper. The diapers were placed on the Courtray mannequin and the ABL was measured and recorded per the procedure supplied by the manufacturer of the mannequin.

XI. Soy Protein Isolate with Surface Tension of Less than 49 mN/in

The surface tensions of solutions of Profam® 781 SPI were tested. Surface tension of solutions at concentrations in the range of 0.05 wt. % to 10 wt. % were in the range of 40 to 49 mN/m at 22° C. The mean value was 43±1.3 mN/m. In contrast to Clarisoy® 100, a 0.5 wt. % to 10 wt. % solids solution of ProFAM® 781 SPI can reduce the surface tension of water to less than 49 mN/m. ProFAM® 781 containing solutions are not spontaneously imbibed by hydrophobic nonwovens, and require special processing (e.g., heating process described in Section IV and below) to uniformly distribute the finish throughout the nonwoven structure. The solutions were prepared by adding with agitation dry powder SPI to distilled water at 75 to 85° C., or about 80° C. The solution was agitated at 80° C. for about 20 to 50 minutes, or about 30 minutes. The solution were added to the fabric using a two-stage dip-and-nip process. The treated fabric was dried and tested using the 4-Hole Drop test described above. The material has an average drop value of 1.5. Surface tension was measured using a Kibron (Parrish, Fla.) Ez Pi Plus instrument which uses the DuNouy maximum pull force method. Table 9 lists the surface tension of the Profam® 781 samples at various weight percentages.

TABLE 9

| wt. % Profam ® 781 | Surface Tension (mN/m) |
|---|---|
| 0.001 | 70.5 |
| 0.01 | 61.8 |
| 0.1 | 55.6 |
| 0.5 | 48.6 |
| 1.0 | 45.2 |
| 2.0 | 43.9 |
| 4.0 | 42.7 |
| 6.0 | 42.5 |
| 8.0 | 42.0 |
| 10.0 | 42.0 |

From the foregoing, it will be observed that numerous modifications and variations can be effected without departing from the true spirit and scope of the novel concept of the present invention. It is to be understood that no limitation with respect to the specific embodiments disclosed herein is intended or should be inferred. The disclosure is intended to cover, by the appended claims, all such modifications as fall within the scope of the claims.

The invention claimed is:

1. A hydrophilic, synthetic sheet comprising:
   a sheet of synthetic material having a first surface;
   where the sheet comprises a hydrophilic finish including molecules of a water-soluble protein dispersed on the first surface;
   where the finish includes substantially no synthetic surfactants;
   where a 0.5-10% aqueous solution of the water-soluble protein has a surface tension of less than 49 milliNewtons per meter (mN/m); and
   the water-soluble protein comprises soy protein isolate.

2. The sheet of claim 1, wherein the finish does not include synthetic materials capable of reducing the surface tension of water below 50 mN/m.

3. The sheet of claim 1, wherein the sheet comprises a nonwoven fabric or a film.

4. The sheet of claim 1, where the sheet is a topsheet of an absorbent article.

5. The sheet of claim 1, wherein the sheet is a distribution-acquisition layer of an absorbent article.

6. The sheet of claim 1, wherein the water-soluble protein comprises a thermally-denatured protein.

7. The sheet of claim 1, wherein a 1.2-10% aqueous solution of the water-soluble protein has a surface tension of less than 49 mN/m.

8. The sheet of claim 1, wherein at least 0.004 grams of the molecules of the water-soluble protein are dispersed on the sheet for each gram of sheet.

9. A disposable absorbent article comprising:
   a topsheet comprising the sheet of claim 1;
   a backsheet; and
   an absorbent core disposed between the topsheet and the backsheet.

10. A disposable absorbent article comprising:
    a topsheet;
    a distribution-acquisition layer comprising the sheet of claim 1;
    a backsheet; and
    an absorbent core disposed between the distribution-acquisition layer and the backsheet.

11. A method of imparting hydrophilic properties to a sheet of polymeric material, the method comprising:
    applying a 0.5-10% aqueous solution of a water-soluble protein having a surface tension of less than 49 milliNewtons per meter (mN/m) to a sheet of polymeric material in an aqueous solution; and
    drying the sheet such that at least a portion of the protein is retained on a surface of the sheet;
    where the aqueous solution is substantially free of synthetic surfactants; and
    where the protein comprises soy protein isolate.

12. A finish for a synthetic nonwoven or film, the finish comprising:
    an 0.5-10% aqueous solution of a water-soluble, thermally-denatured protein, the solution having a surface tension less than 49 milliNewtons per meter (mN/m);
    where the aqueous solution is substantially free of synthetic surfactants; and
    where the protein comprises soy protein isolate.

* * * * *